(12) United States Patent
Kumar Karn et al.

(10) Patent No.: US 12,148,531 B2
(45) Date of Patent: Nov. 19, 2024

(54) GENERATING REASONS FOR IMAGING STUDIES

(71) Applicant: Siemens Medical Solutions USA, Inc., Malvern, PA (US)

(72) Inventors: Sanjeev Kumar Karn, Plainsboro Township, NJ (US); Oladimeji Farri, Upper Saddle River, NJ (US); Jonathan Darer, Lewisburg, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 329 days.

(21) Appl. No.: 17/303,919

(22) Filed: Jun. 10, 2021

(65) Prior Publication Data
US 2022/0293267 A1  Sep. 15, 2022

Related U.S. Application Data

(60) Provisional application No. 63/161,031, filed on Mar. 15, 2021.

(51) Int. Cl.
| | | |
|---|---|---|
| *G06N 20/00* | (2019.01) | |
| *G06F 40/20* | (2020.01) | |
| *G06F 40/205* | (2020.01) | |
| *G16H 10/60* | (2018.01) | |
| *G16H 30/20* | (2018.01) | |

(Continued)

(52) U.S. Cl.
CPC ........... *G16H 50/20* (2018.01); *G06F 40/205* (2020.01); *G06N 20/00* (2019.01); *G16H 70/60* (2018.01); *G16H 10/60* (2018.01); *G16H 30/20* (2018.01)

(58) Field of Classification Search
CPC ........ G16H 10/60; G16H 50/20; G16H 70/20; G06Q 10/063; G06F 40/129; G06N 3/006; G16B 40/20
See application file for complete search history.

(56) References Cited

U.S. PATENT DOCUMENTS

| | | | | |
|---|---|---|---|---|
| 11,120,899 B1 * | 9/2021 | Rai | ....................... | G06F 40/295 |
| 2012/0329015 A1 * | 12/2012 | Thesman | ............... | G16H 70/20 |
| | | | | 707/812 |

(Continued)

OTHER PUBLICATIONS

Śniegula, Anna, Aneta Poniszewska-Maranda, and Łukąsz Chomatek. "Study of Named Entity Recognition methods in biomedical field." Procedia Computer Science 160 (2019): 260-265.

(Continued)

*Primary Examiner* — Saba Dagnew (57) ABSTRACT

A framework for generating reasons for imaging studies. An extractor, including a reinforcement learning agent, is trained to select one or more relevant sentences from the training histories of present illness. An abstractor is further pre-trained to generate one or more reasons for study from the one or more relevant sentences. An entity linking system is pre-trained using medical text corpora to map one or more mentions in the one or more reasons for study to one or more standardized medical entities for predicting one or more diagnoses. The reinforcement learning agent may then be re-trained using one or more rewards generated by the entity linking system. One or more reasons for study may be generated from a current history of present illness using the trained extractor, abstractor and entity linking system.

20 Claims, 6 Drawing Sheets

(51) Int. Cl.
*G16H 50/20* (2018.01)
*G16H 70/60* (2018.01)

(56) References Cited

U.S. PATENT DOCUMENTS

| | | | | |
|---|---|---|---|---|
| 2013/0226619 | A1* | 8/2013 | Takeuchi | G06F 40/129 |
| | | | | 705/3 |
| 2015/0347521 | A1* | 12/2015 | Zhu | G06F 40/30 |
| | | | | 715/230 |
| 2018/0068083 | A1* | 3/2018 | Cohen | G16B 40/20 |
| 2018/0373844 | A1* | 12/2018 | Ferrandez-Escamez | |
| | | | | G16H 50/20 |
| 2019/0355471 | A1* | 11/2019 | Peng | G06N 3/006 |
| 2019/0362835 | A1* | 11/2019 | Sreenivasan | G06N 3/044 |
| 2020/0097808 | A1* | 3/2020 | Thomas | G06Q 10/063 |
| 2020/0176098 | A1* | 6/2020 | Lucas | G16H 10/60 |
| 2021/0241871 | A1* | 8/2021 | Burnett | G16H 70/60 |
| 2023/0377748 | A1* | 11/2023 | Yang | G06N 3/08 |

OTHER PUBLICATIONS

Devlin, Jacob, et al. "Bert: Pre-training of deep bidirectional transformers for language understanding." arXiv preprint arXiv:1810.04805 (2018).
Vaswani, Ashish, et al. "Attention is all you need." arXiv preprint arXiv:1706.03762 (2017).
Zhang, Jingqing, et al. "Pegasus: Pre-training with extracted gap-sentences for abstractive summarization." International Conference on Machine Learning. PMLR, 2020.
Hsu, Wan-Ting, et al. "A unified model for extractive and abstractive summarization using inconsistency loss." arXiv preprint arXiv:1805.06266 (2018).

\* cited by examiner

102

1. "This is an 81-year-old female with a history of emphysema (not on home O2), who presents with three days of shortness of breath thought by her primary care doctor to be a COPD flare",
2. "Two days prior to admission, she was started on a prednisone taper and one day prior to admission she required oxygen at home in order to maintain oxygen saturation greater than 90%",
3. "She has also been on levofloxacin and nebulizers, and was not getting better, and presented to the Emergency Room",
4. "In the Emergency Room, her oxygen saturation was 100% on CPAP",
5. "She was not able to be weaned off of this despite nebulizer treatment and Solu-Medrol 125 mg IV x2",
6. "Review of systems is negative for the following: Fevers, chills, nausea, vomiting, night sweats, change in weight, gastrointestinal complaints, neurologic changes, rashes, palpitations, orthopnea",
7. "Is positive for the following: Chest pressure occasionally with shortness of breath with exertion, some shortness of breath that is positionally related, but is improved with nebulizer treatment"

⎬ 104

1. "r/o infiltrate failure"
2. "evaluate for PNA, consolidation, effusion."
3. "ntg placement"
4. "S/P ett placement. Assess prper placement."
5. "place NGT"
6. "eval for pulm effusions vs infiltrate"
7. "intubated, asses for interval change"
8. "evaluate for evidence of tracheal stent position and evaluate for pna
9. "evid of bronchial stent migration? evid of PNA/CHF?"

106

- Lung infiltrates (C217U),
- Pneumonia (C252U),
- Pleural effusion (C247U),
- Endotracheal tube assessment (C410U),
- Nasogastric tube placement (W74U),
- Tracheal or endobronchial stent (N56U)

GENERATING REASONS FOR IMAGING STUDIES

CROSS-REFERENCE TO RELATED APPLICATION

The present application claims the benefit of U.S. provisional application No. 63/161,031 filed Mar. 15, 2021, the entire contents of which are herein incorporated by reference.

TECHNICAL FIELD

The present disclosure generally relates to digital data processing, and more particularly to generating reasons for imaging studies.

BACKGROUND

Physicians typically order radiology imaging studies to confirm certain abnormalities/disorders during patient care. The physician's reasons for ordering the radiology imaging studies (RFS) or reasons for examinations (RFE) are typically found in an electronic medical record (EMR), which contains various health-related information associated with a specific patient in a hospital stay. Such health-related information may include a history of present illness (HPI), as well as reasons for various radiology imaging studies ordered by physician for that patient at one hospital stay.

It is observed that 10-30% of such physician orders of radiology imaging studies require revision by radiologists due to various errors. The most frequent issue is the misalignment between the reason for the imaging study and the diagnosis to be confirmed. Revising the imaging orders often means radiologists need to review physician progress notes within the EMR to obtain the correct reason for study (RFS). This task can be time-consuming and may be perceived as an interruption to the usual radiology workflow. Additionally, the communication breakdown between the ordering physician and the radiologist may contribute to delays in providing care, leading to patient dissatisfaction. Furthermore, if the radiologist does not revise the incorrect orders and act on the original requests, associated errors in clinical decisions will impact the hospital revenue cycle and can result in significant amounts of unreimbursed care services.

SUMMARY

Described herein is a framework for generating reasons for imaging studies. According to one aspect, an extractor, including a reinforcement learning agent, is trained to select one or more relevant sentences from the training histories of present illness. An abstractor is further pre-trained to generate one or more reasons for study from the one or more relevant sentences. An entity linking system is pre-trained using medical text corpora to map one or more mentions in the one or more reasons for study to one or more standardized medical entities for predicting one or more diagnoses. The reinforcement learning agent may then be re-trained using one or more rewards generated by the entity linking system. One or more reasons for study may be generated from a current history of present illness using the trained extractor, abstractor and entity linking system.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings.

FIG. 1 shows an exemplary electronic medical record (EMR);

DETAILED DESCRIPTION

In the following description, numerous specific details are set forth such as examples of specific components, devices, methods, etc., in order to provide a thorough understanding of implementations of the present framework. It will be apparent, however, to one skilled in the art that these specific details need not be employed to practice implementations of the present framework. In other instances, well-known materials or methods have not been described in detail in order to avoid unnecessarily obscuring implementations of the present framework. While the present framework is susceptible to various modifications and alternative forms, specific embodiments thereof are shown by way of example in the drawings and will herein be described in detail. It should be understood, however, that there is no intent to limit the invention to the particular forms disclosed; on the contrary, the intention is to cover all modifications, equivalents, and alternatives falling within the spirit and scope of the invention. Furthermore, for ease of understanding, certain method steps are delineated as separate steps; however, these separately delineated steps should not be construed as necessarily order dependent in their performance.

Unless stated otherwise as apparent from the following discussion, it will be appreciated that terms such as "segmenting," "generating," "registering," "determining," "aligning," "positioning," "processing," "computing," "selecting," "estimating," "detecting," "tracking" or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, implementations of the present framework are not described with reference to any particular programming language. It will be appreciated that a variety of programming languages may be used.

Medical named entity recognition (NER) is a well-known natural language processing (NLP) technique. Medical NER may be implemented using traditional machine learning techniques, such as hidden Markov model (HMI), conditional random fields (CRF), more recent deep learning techniques (e.g., recurrent neural networks (RNN), long short term memory (LSTM) etc.), or combination of techniques (e.g. LSTM-CRF). Medical NER tasks often involve extracting single or multiple clinical terms from text. A direct application of medical NER on HPI will recognize many explicitly mentioned entity types, such as symptoms, findings or syndromes/diseases. However, medical NER will not recognize other implicitly associated suspected conditions (and corresponding entity types) that require attention and diagnosis, such as pulmonary infiltrate, pneumonia, consolidation, effusion, etc.

Text summarization is an NLP task of producing a short version of a source document while preserving its salient information. There are two types of text summarization: extractive and abstractive. Extractive text summarization involves pulling salient text or keyphrases from the source document and compiling the salient text to make a summary. Applying extractive summarization on medical text helps to identify only relevant text and corresponding entity types. However, like Medical NER, extractive summarization misses identifying suspected conditions. Abstractive summarization techniques generate the summary bottom up and entail paraphrasing and shortening parts of the source document. Abstractive text summarization algorithms create new content (e.g., inferred text) that relays the most useful information from the original text. Therefore, abstraction performs better than extraction, because it can generate suspected conditions/diagnoses. However, abstractive summarization requires a significant amount of labelled training data and this magnifies with the increase in level of abstraction (low overlap) between source text and target summary. For radiology examinations, translating HPI to reasons for study (RFS) is highly abstractive and also lacks sufficient labels.

FIG. 1 shows an exemplary EMR 102. The top section 104 shows a history of present illness (HPI) during a hospital stay. The middle section 106 shows a list of reasons for various radiology imaging studies ordered by physician for that patient at one hospital stay. The bottom section 108 lists standardized signs, symptoms and diagnoses that are mentioned in the imaging studies for which the hospital raises reimbursement requests. The indications/diagnoses for the imaging study (shown in middle section 106) require a strong understanding of signs/symptoms in the HPI (shown in upper section 104). For example, r/o infiltrate (i.e., suspicion of pulmonary infiltrate) can be inferred from points 1 and 7 of the observed HPI in section 104. Similarly, inadequate ventilation or oxygenation from points 1, 2, and 7 of the observed HPI in section 104 imply usage of NGT (nasogastric tube) and its placement verification as shown in section 106.

Thus, unlike many abstractive summarization tasks, RFS are a collection of highly abstractive singular phrases or sentences, such as "evaluate for PNA, consolidation, effusion" or "r/o infiltrate failure", or even just single word "infiltrate". Automatically generating such abstractive text requires document level inference, abstraction and paraphrasing. Each physician progress note typically has sections of text with main symptoms and diseases. For example, point 1 in the HPI (shown in upper section 104) with text " . . . with a history of emphysema (not on home O2), who presents with three days of shortness of breath thought by her primary care doctor to be a COPD flare", guides physicians to order an exam and give a reason (e.g., "evaluate for PNA, consolidation, effusion"). It becomes easy for the model to generate relevant RFS if it is guided to focus on such sections of text in the HPI. Additionally, it is equally important for the RFS generation system to be intelligent enough to disambiguate abbreviated medical terms, such as COPD (chronic obstructive pulmonary disease) and R/O (rule out), and knowledgeable about the subtleties associated with medical terms.

A framework for automatically generating reasons for imaging studies (RFS) is presented herein. The present framework employs a two-step summarization method (i.e., extractive followed by abstractive) and divides the overall summarization method into two subtasks: distilling important texts (extractive) followed by paraphrasing them (abstractive). However, overlap between HPI-RFS is so low that simple overlaps between RFS and HPI are insufficient to guide the two-step model. Therefore, the present framework utilizes an external medical knowledge base through an entity linking system. This entity linking system links diagnoses in the generated text to a standard ontology and validates the number of accurately mapped diagnoses. Thus, it addresses the variations in medical terms and indirectly measures the relevancy of generated text. The entity linking system is integrated into the two-step summarization module through a reinforcement learning (RL) technique. Rewards for the reinforcement learning are determined by evaluating the quality of the RFS generated by the abstractor using entity linking.

The present framework address the issues of misalignment between diagnoses and imaging study requests, and minimizes delay in providing care by automatically generating RFS using the HPI. The present framework combines both extractive and abstractive text summarization techniques and also employs entity-linking in order to ensure that the right context related to medical terms in RFS and suspected conditions are included in the generated results. Pretraining of individual components addresses the issue of compiling a large number of HPI-RFS pairs for training a highly abstractive system, enabling the framework to learn from a small size of such pairs. These and other features and advantages will be described in more details herein.

Figure 2:
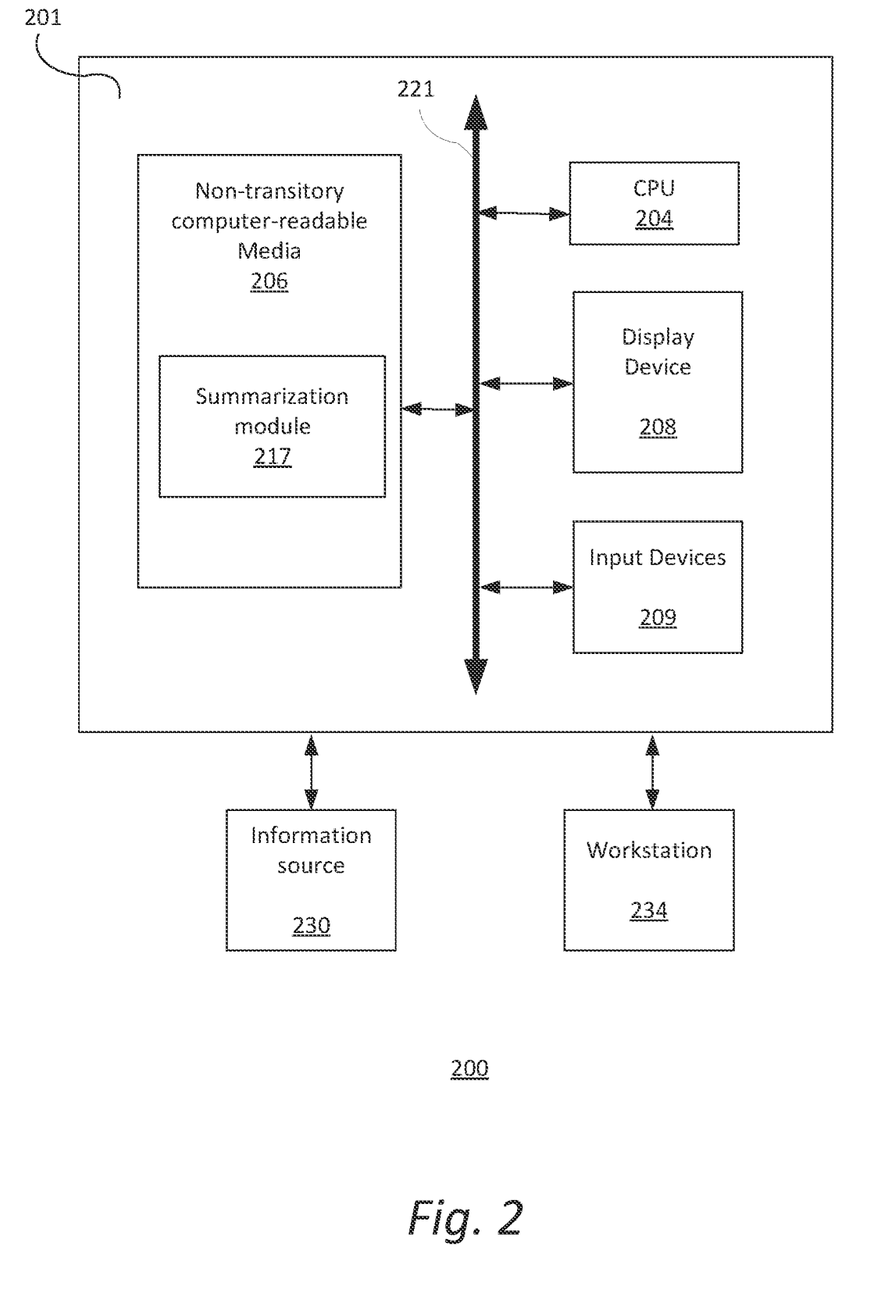
FIG. 2 is a block diagram illustrating an exemplary system.

FIG. 2 is a block diagram illustrating an exemplary system 200. The system 200 includes a computer system 201 for implementing the framework as described herein. In some implementations, computer system 201 operates as a standalone device. In other implementations, computer system 201 may be connected (e.g., using a network) to other machines, such as information source 230 and workstation 234. In a networked deployment, computer system 201 may operate in the capacity of a server (e.g., thin-client server), a cloud computing platform, a client user machine in server-client user network environment, or as a peer machine in a peer-to-peer (or distributed) network environment.

In some implementations, computer system 201 comprises a processor or central processing unit (CPU) 204 coupled to one or more non-transitory computer-readable media 206 (e.g., computer storage or memory), display device 208 (e.g., monitor) and various input devices 209 (e.g., mouse or keyboard) via an input-output interface 221. Computer system 201 may further include support circuits such as a cache, a power supply, clock circuits and a communications bus. Various other peripheral devices, such as additional data storage devices and printing devices, may also be connected to the computer system 201.

The present technology may be implemented in various forms of hardware, software, firmware, special purpose processors, or a combination thereof, either as part of the microinstruction code or as part of an application program or software product, or a combination thereof, which is executed via the operating system. In some implementations, the techniques described herein are implemented as computer-readable program code tangibly embodied in non-transitory computer-readable media 206. In particular, the present techniques may be implemented by summarization module 217.

Non-transitory computer-readable media 206 may include random access memory (RAM), read-only memory (ROM), magnetic floppy disk, flash memory, and other types of memories, or a combination thereof. The computer-readable program code is executed by CPU 204 to process medical data retrieved from, for example, information source 230. As such, the computer system 201 is a general-purpose computer system that becomes a specific purpose computer system when executing the computer-readable program code. The computer-readable program code is not intended to be limited to any particular programming language and implementation thereof. It will be appreciated that a variety of programming languages and coding thereof may be used to implement the teachings of the disclosure contained herein.

The same or different computer-readable media 206 may be used for storing a database (or dataset). Such data may also be stored in external information source 230 or other memories. Information source 230 may store medical images acquired by a radiology imaging device (e.g., MR or CT scanner) as well as electronic medical records (EMRs) and other types of information. Such EMRs may include health-related information associated with specific patients, including histories of present illness (HPIs). Information source 230 may be implemented using a database management system (DBMS) managed by the CPU 204 and residing on a memory, such as a hard disk, RAM, or removable media. Information source 230 may be implemented on one or more additional computer systems. For example, information source 230 may include a data warehouse system residing on a separate computer system, a cloud platform or system, an EMR system, or any other hospital, medical institution, medical office, testing facility, pharmacy or other medical patient record storage system.

The workstation 234 may include a computer and appropriate peripherals, such as a keyboard and display device, and can be operated in conjunction with the entire system 200. For example, the workstation 234 may communicate directly or indirectly with the information source 230 so that medical information may be displayed at the workstation 234 and viewed on a display device. The workstation 234 may include a graphical user interface to receive user input via an input device (e.g., keyboard, mouse, touch screen voice or video recognition interface, etc.).

It is to be further understood that, because some of the constituent system components and method steps depicted in the accompanying figures can be implemented in software, the actual connections between the systems components (or the process steps) may differ depending upon the manner in which the present framework is programmed. Given the teachings provided herein, one of ordinary skill in the related art will be able to contemplate these and similar implementations or configurations of the present framework.

Figure 3:
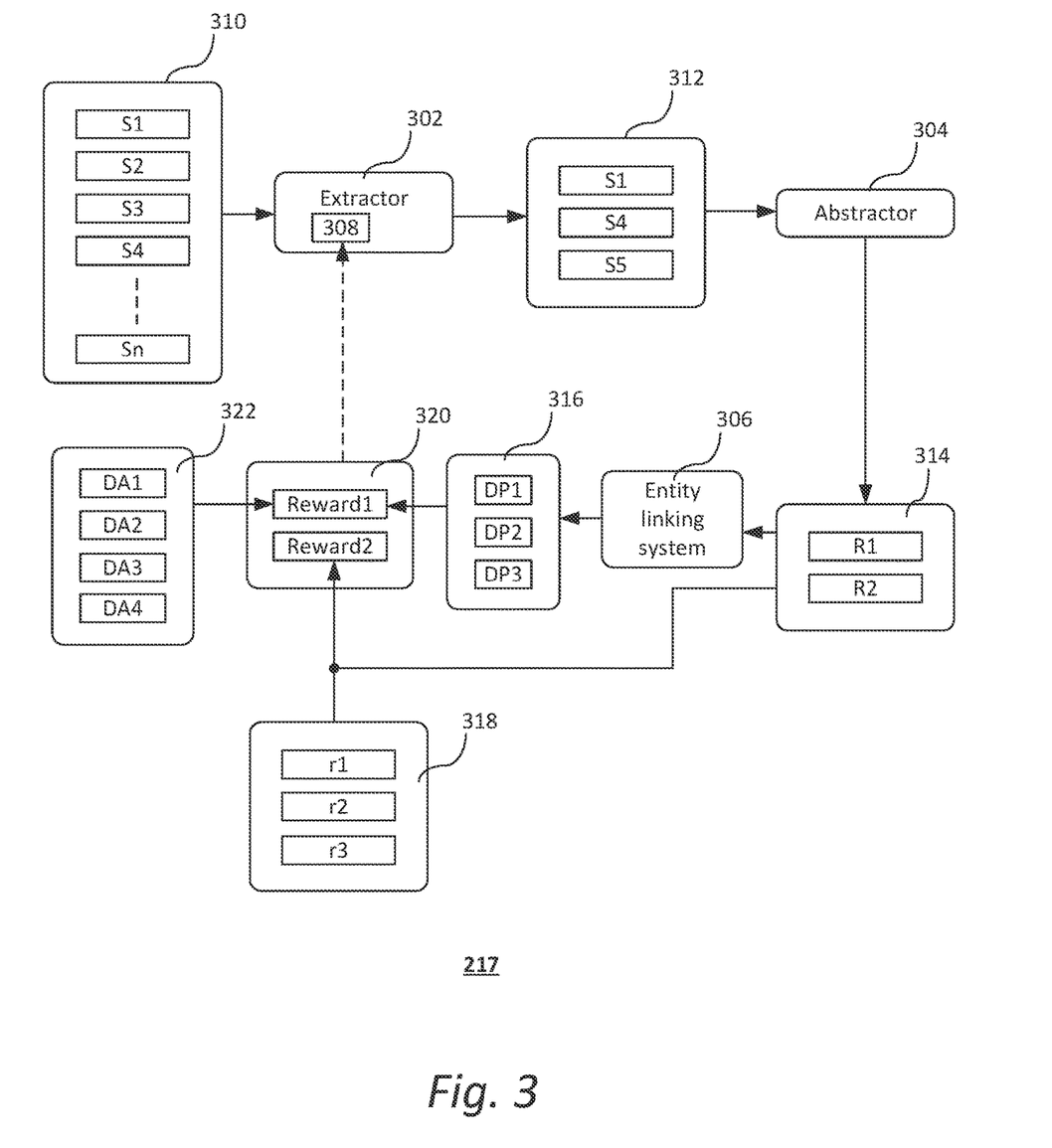
FIG. 3 shows an exemplary summarization module.

FIG. 3 shows an exemplary summarization module 217. Summarization module 217 includes an extractor 302, an abstractor 304, an entity linking system 306 and a reinforcement learning (RL) agent 308. Extractor 302 receives as input a discharge summary 310 or any other EMR of a specific patient. The discharge summary 310 includes a history of present illness (HPI), that is made up of multiple sentences S1, S2, S3, S4, Sn. Each sentence S includes one or more words that describe the illness. Extractor 302 is trained to extract relevant sentences (e.g., S1, S4, S5) 312 out of the HPI. Abstractor 304 is trained to generate reasons for imaging study (RFS) 314 from the extracted sentences 312. RFS 314 includes one or more reasons (e.g., R1, R2) for ordering a radiology study, examination or report for the patient.

The generated RFS 314 is passed through an entity linking system 306. Entity linking system 306 is an unsupervised zero or few shot entity-linking model that does not require a separate entity-linking corpus for training, which is an expensive and time-consuming process. The entity linking system 306 takes the RFS 314, detects mentions and maps them to a dictionary (or ontology) of standard medical entities (e.g., Systematized Nomenclature of Medicine or SNOMED) A "mention" as used herein is a reference or representation of an entity or an object that appeared in texts. The entity linking system 306 finds all the normalized/standardized entities associated with the RFS 314. Entity linking system 306 includes a pre-trained transformer-based contextual language model that obtains representations of mention text and windows of text on left and right of the mention. Entity linking system 306 then combines these representations and learns to map it to appropriate standardized entities in the dictionary. Such entities are output as predicted diagnoses (e.g., DP1, DP2, DP3) 316.

The reinforcement learning (RL) agent 308 may be implemented in the extractor 302, and is trained using actor-critic reinforcement learning technique. The aim of the reinforcement learning (RL) agent 308 is to select relevant sentences 312 from the source HPI 310 and is rewarded based on the quality of generated RFS 314 from the abstractor 304. In some implementations, entity linking system 306 measures the overlap (e.g., percentage overlap) between the generated predicted diagnoses 316 and the reference or actual diagnoses (e.g., DA1, DA2, DA3, DA4) 322 to generate the reward (e.g., Reward1) 320 that is sent to the reinforcement learning (RL) agent 308. Another type of reward (e.g., Reward2) 320 may be generated based on the overlap between the actual RFS (e.g., r1, r2, r3) 318 and the RFS 314 generated by the abstractor 304. Other methods of reward generation may also be used.

Figure 4:
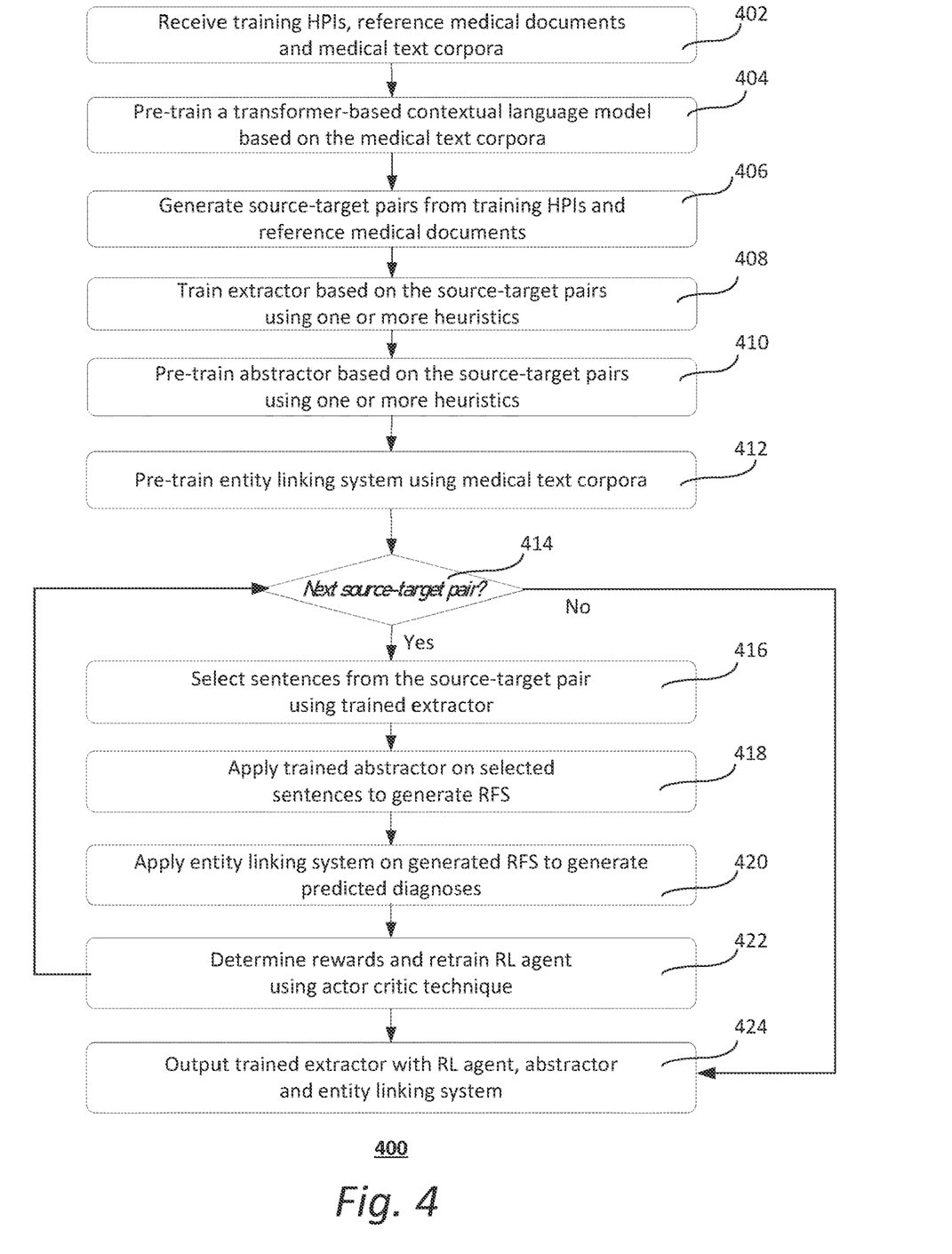
FIG. 4 shows an exemplary method of training a summarization module to generate reasons for imaging studies.

FIG. 4 shows an exemplary method 400 of training a summarization module to generate reasons for imaging studies. It should be understood that the steps of the method 400 may be performed in the order shown or a different order. Additional, different, or fewer steps may also be provided. Further, the method 400 may be implemented with the system 200 of FIG. 2, the summarization module 217 of FIG. 3, a different system, or a combination thereof.

At 402, summarization module 217 receives training HPIs, reference medical documents and a medical text corpora. The training HPIs may be extracted from discharge summaries, physician progress notes, EMRs or other medical documents for specific patients. The reference medical documents are used for evaluating the quality of the RFS generated by the abstractor 304. In some implementations, the reference medical documents include actual diagnoses and/or radiology reports with actual RFS.

The medical text corpora include texts collected with a focus on the medical domains. The medical text corpora may be compiled out of free text from sources (e.g., the Web) by using regular expressions created based on entries in standard medical ontologies (e.g., Systematized Nomenclature of Medicine or SNOMED). The medical text corpora may be preprocessed by using natural language processing tools, such as Stanford CoreNLP or ScispaCy. See, for example, Manning, Christopher D., Mihai Surdeanu, John Bauer, Jenny Finkel, Steven J. Bethard, and David McClosky, *The*

Stanford CoreNLP Natural Language Processing Toolkit, Proceedings of the 52nd Annual Meeting of the Association for Computational Linguistics: System Demonstrations, pp. 55-60 (2014); Neumann, Mark, Daniel King, Iz Beltagy and Waleed Ammar, *ScispaCy: Fast and Robust Models for Biomedical Natural Language Processing*, ArXiv abs/ 1902.07669 (2019).

At 404, a transformer-based contextual language model is pre-trained based on the medical text corpora. The transformer-based contextual language model may be used in extractor 302 and/or abstractor 304. The transformer-based contextual language model is an unsupervised language representation deep learning model that is trained based on the medical text corpora to map input text to representations. See, for example, Ashish Vaswani et al., *Attention is all you need*, Advances in Neural Information Processing Systems (NIPS) 2017, which is herein incorporated by reference.

Figure 5:
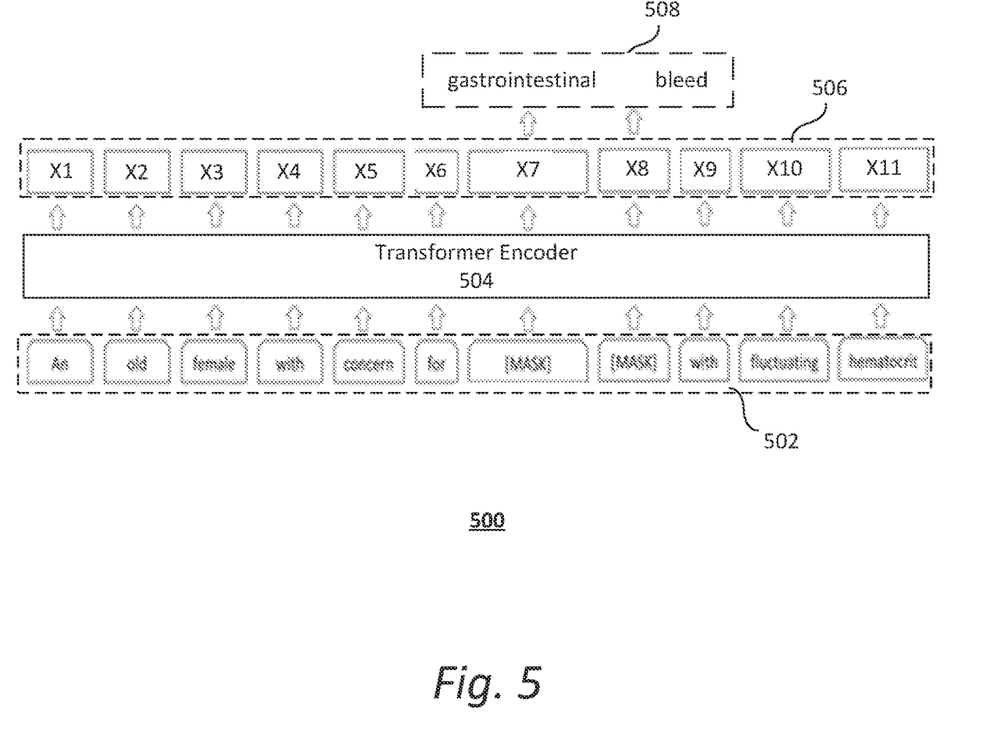
FIG. 5 illustrates pre-training of a Bidirectional Encoder Representations from Transformers (BERT) masked language model (MLM)

One example of a transformer-based contextual language model is the Bidirectional Encoder Representations from Transformers (BERT). See, for example, Jacob Devlin et al., *BERT: Pre-training of deep bidirectional transformers for language understanding*, North American Association for Computational Linguistics (NAACL) 2019, which is herein incorporated by reference. BERT optimizes two training objectives—masked language model (MLM) and next sentence prediction (NSP). FIG. 5 illustrates a pre-training process 500 of a BERT masked language model (MLM) 504 using a large corpus of medical text 502 to generate words and sentences in vector representations 506. Output X7 and X8 are masked words "gastrointestinal" and "bleed" 508 respectively.

Returning to FIG. 4, at 406, summarization module 217 generates source-target pairs from the training HPIs and reference medical documents. Each source-target pair includes a HPI and a corresponding actual RFS associated with a specific patient and a specific hospital stay. The actual RFS may be extracted from a radiology report in the reference medical documents.

At 408, extractor 302 is trained based on the source-target pairs using one or more heuristics. Extractor 302 is trained to extract relevant sentences out of the HPIs. Heuristics that may be used to train the extractor 302 include, for example, using the overlap between indications in the HPIs and the actual RFS to guide the training.

At 410, abstractor 304 is pre-trained based on the source-target pairs using one or more heuristics to generate RFS from the sentences selected by extractor 302. The one or more heuristics include, for example, token-overlap above a predetermined threshold to guide the pre-training. In some implementations, abstractor 304 is a deep transformer-based encoder-decoder model, where the encoder and decoder weights are pretrained with self-supervised pre-training designed for abstractive text summarization. See, for example, Zhang, Jingqing, et al. "Pegasus: Pre-training with extracted gap-sentences for abstractive summarization." arXiv preprint arXiv:1912.08777 (2019), which is herein incorporated by reference.

Pre-training tailored for abstractive text summarization selects and masks whole sentences from documents and concatenates the gap-sentences into a pseudo-summary. This training process is known as gap sentences generation (GSG) and has a hyper-parameter gap sentences ratio (GSR). The GSR refers to the ratio of the number of selected gap sentences to the total number of sentences in the document, which is similar to mask rate in MLM. In abstractor 304, both gap sentences and GSR are selected using the medical knowledge in the pre-training medical text corpora. Gap sentences should have mention of at least one entity from a curated list of allowed medical entities (e.g., symptoms).

At 412, entity linking system 306 is pre-trained using medical text corpora. Entity linking system 306 is pre-trained to detect one or more mentions in the RFS generated by abstractor 304 and map the one or more mentions to one or more standardized medical entities in the medical text corpora, so as to predict one or more diagnoses 316. Entity linking system 306 may include a pre-trained transformer-based contextual language model. Mention text and windows of text on the left and right of each mention are passed through a pre-trained contextual language model to obtain representations. Entity linking system 306 then combines these representations and learns to map it to appropriate entities in the dictionary (or ontology). Entity linking system 306 provides unsupervised zero or few shot entity linking, since it is only trained on a corpus of different biological domains and directly applied to selectively map RFS mentions to standard medical entities in a standard medical ontology.

A mention detection component in the entity linking system 306 may be trained using minimal supervision, using, for instance, vocabulary from SNOMED and building rules. Machine learning techniques, such as semi-supervised learning and transfer learning, may also be used. Similarly, a linking component in the entity linking system 306 may also be trained using zero or few shot learning techniques in combination with transfer learning. There are several related corpora for transfer-learning, such as The National Center for Biotechnology Information (NCBI) Disease Corpus, which is a resource for disease name recognition and concept normalization.

At 414, it is determined if there is any source-target pair to be processed. If there is, the method proceeds to 416 to process the next source-target pair as the current source-target pair. If there are no further source-target pair to be processed, the method proceeds to 424.

At 416, sentences are selected from the current source-target pair using the trained extractor 302. The trained extractor provides an RL agent 308. The aim of the RL agent 308 is to select relevant sentences from the source HPI, and receive a feedback of rewards based on the quality of the RFS generated by the abstractor 304.

At 418, the trained abstractor 304 is applied on the selected sentences to generate RFS. The RFS includes one or more paraphrases of the selected sentences to convey the most useful information from the original text.

At 420, entity linking system 306 is applied to the generated RFS to generate predicted diagnoses. Basically, since several medical terms are expressed in different forms (e.g., "pulmonary infiltrates" is also written as "infiltrates" and "Pneumonia" as "PNM"), this implies that the model can generate a different form of an indication in HPI than the reference RFS. Entity linking system 306 detects mentions in the generated RFS, maps the mentions to normalized (or standardized) entities using a dictionary (or ontology) and generates predicted diagnoses 316 as output. In other words, the predicted diagnoses are indications in standard ontology (e.g., SNOMED) that are determined by linking relevant phrases in the generated RFS using the entity linking system 306.

At 422, entity linking system 306 determines rewards and re-trains the RL agent 308 using an actor critic technique. The actor critic technique is a temporal difference (TD) method that has a separate memory structure (i.e., actor) to explicitly represent the policy independent of the value function (i.e., critic). The rewards for the value function may be determined by measuring the overlap (e.g., percentage overlap) between the predicted diagnoses and actual diagnoses extracted from the reference medical documents. Additionally, the rewards 320 may also be determined by measuring the overlap (e.g., percentage overlap) between the generated RFS and the actual RFS extracted from the reference medical documents.

At 424, the trained extractor 302 with the trained RL agent 308, the trained abstractor 304 and trained entity linking system 306 are output. The trained extractor 302, trained RL agent 308, trained abstractor 304 and trained entity linking system 306 may be applied to a current history of present illness associated with a current patient to generate one or more reasons for study.

Figure 6:
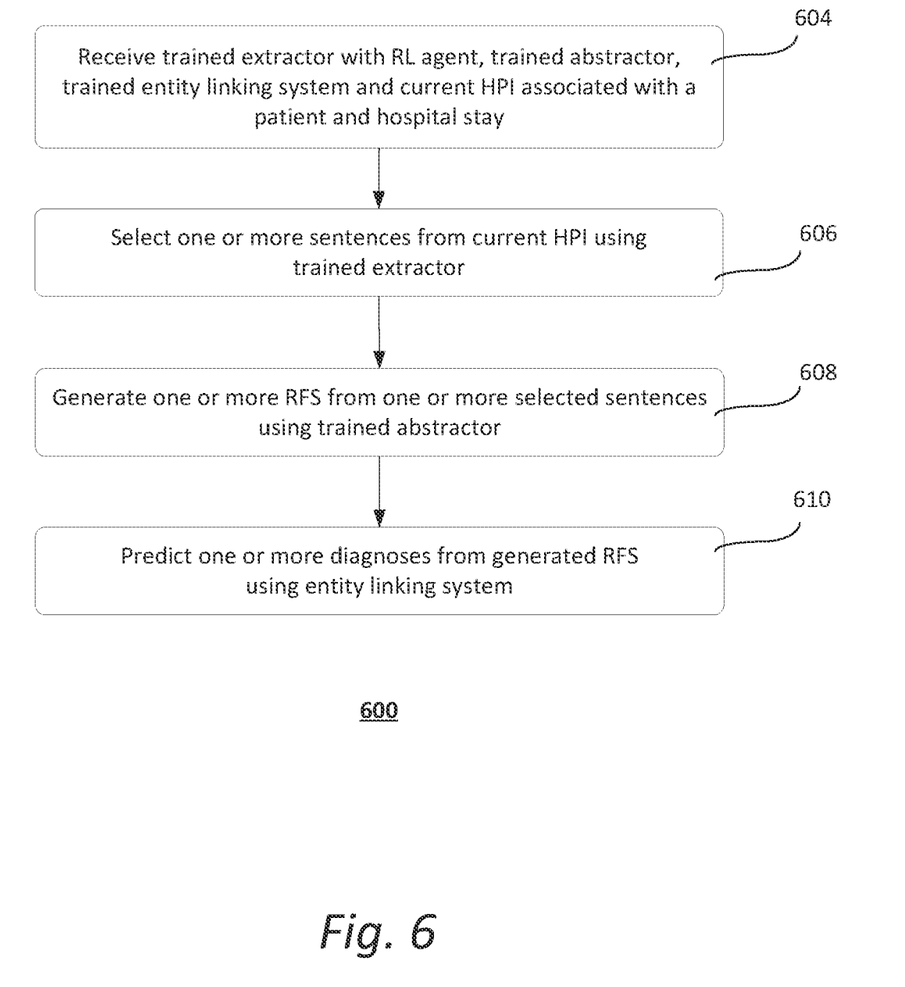
FIG. 6 shows an exemplary method of generating reasons for imaging studies.

FIG. 6 shows an exemplary method 600 of generating reasons for imaging studies. It should be understood that the steps of the method 600 may be performed in the order shown or a different order. Additional, different, or fewer steps may also be provided. Further, the method 600 may be implemented with the system 200 of FIG. 2, the summarization module 217 of FIG. 3, a different system, or a combination thereof.

At 604, the trained extractor 302 with the trained RL agent 308, the trained abstractor 304, the trained entity linking system 306 and a current HPI are received. The current HPI may be extracted from a medical document that is associated with a specific patient for a specific hospital stay. The current medical document may be, for example, a discharge summary, physician progress notes or other EMR.

At 606, the trained extractor 302 selects one or more sentences from the current HPI.

At 608, the trained abstractor 304 generates one or more RFS from the one or more selected sentences.

At 610, the entity linking system 306 predicts one or more diagnoses from the one or more generated RFS. More particularly, the entity linking system 306 detects one or more mentions in the generated RFS and maps them to standardized entities in a dictionary (or ontology) to compile one or more predicted diagnoses.

While the present framework has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

What is claimed is:

1. A medical text summarization system, comprising:
    a non-transitory memory device for storing computer readable program code; and
    a processor device in communication with the memory device, the processor device being operative with the computer readable program code to perform steps including
        receiving training histories of present illness, reference medical documents and medical text corpora,
        training, based on the training histories of present illness and the reference medical documents, an extractor that selects one or more relevant sentences from the training histories of present illness, wherein the extractor comprises a reinforcement learning agent,
        pre-training, based on the training histories of present illness and the reference medical documents, an abstractor that generates one or more first reasons for study from the one or more relevant sentences selected by the extractor, wherein the one or more first reasons for study comprise one or more paraphrases of the one or more relevant sentences,
        pre-training an entity linking system using the medical text corpora to map one or more mentions in the one or more first reasons for study to one or more standardized entities for predicting one or more diagnoses,
        re-training, based on the training histories of present illness and the reference medical documents, the reinforcement learning agent using one or more rewards generated by the entity linking system by evaluating quality of the one or more first reasons for study, and
        generating one or more second reasons for study from a current history of present illness using the trained extractor, the pre-trained abstractor and the pre-trained entity linking system.

2. The medical text summarization system of claim 1 wherein the processor device is operative with the computer readable program code to generate source-target pairs from the training histories of present illness and the reference medical documents for training the extractor and pre-training the abstractor.

3. The medical text summarization system of claim 1 wherein the processor device is operative with the computer readable program code to pre-train a transformer-based contextual language model using the medical text corpora.

4. The medical text summarization system of claim 3 wherein the transformer-based contextual language model is used in the extractor, the abstractor, or a combination thereof.

5. The medical text summarization system of claim 1 wherein the processor device is operative with the computer readable program code to train the extractor using one or more heuristics.

6. The medical text summarization system of claim 1 wherein the processor device is operative with the computer readable program code to pre-train the abstractor using one or more heuristics.

7. The medical text summarization system of claim 2 wherein the processor device is operative with the computer readable program code to re-train the reinforcement learning agent by
    selecting, by the extractor, one or more sentences from at least one of the source-target pairs,
    generating, by the abstractor, one or more reasons for study from the selected one or more sentences,
    predicting, by the entity linking system, one or more diagnoses from the generated one or more reasons for study, and
    determining, by the entity linking system, the one or more rewards for re-training the reinforcement learning agent using an actor critic technique.

8. The medical text summarization system of claim 7 wherein the processor device is operative with the computer readable program code to determine the one or more rewards by measuring an overlap between the one or more diagnoses predicted by the entity linking system and reference diagnoses extracted from the reference medical documents.

9. The medical text summarization system of claim 7 wherein the processor device is operative with the computer readable program code to determine the one or more rewards by measuring an overlap between the one or more reasons for study generated by the abstractor and one or more actual reasons for study extracted from the reference medical documents.

10. A method of medical text summarization, comprising:
- receiving an extractor, an abstractor, an entity linking system and a current history of present illness;
- selecting, using the extractor, one or more sentences from the current history of present illness, wherein the extractor includes a reinforcement learning agent that receives a feedback of one or more rewards from the entity linking system, wherein the one or more rewards are generated by evaluating quality of one or more first reasons for study generated by the abstractor;
- generating, using the abstractor, one or more second reasons for study from the one or more sentences selected by the extractor, wherein the one or more second reasons for study comprise one or more paraphrases of the one or more sentences; and
- predicting, using the entity linking system, one or more diagnoses from the one or more second reasons for study generated by the abstractor.

11. The method of claim 10 further comprises extracting the current history of present illness from a current medical document associated with a specific patient.

12. The method of claim 10 wherein predicting the one or more diagnoses comprises mapping one or more mentions in the one or more generated second reasons for study to one or more standardized entities.

13. The method of claim 10 further comprises pre-training a transformer-based contextual language model using medical text corpora for use in the trained extractor, the pre-trained abstractor, or a combination thereof.

14. The method of claim 10 further comprises training the extractor using one or more heuristics.

15. The method of claim 10 further comprises pre-training the abstractor using one or more heuristics.

16. The method of claim 10 further comprises re-training the reinforcement learning agent using one or more rewards generated by the entity linking system.

17. The method of claim 16 wherein re-training the reinforcement learning agent comprises:
- selecting, by the extractor, one or more sentences from at least one source-target pair;
- generating, by the abstractor, one or more reasons for study from the selected one or more sentences;
- predicting, by the entity linking system, one or more diagnoses from the generated one or more reasons for study; and
- determining, by the entity linking system, the one or more rewards for re-training the reinforcement learning agent using an actor critic technique.

18. The method of claim 17 further comprises determining the one or more rewards by measuring an overlap between the one or more diagnoses predicted by the entity linking system and reference diagnoses.

19. The method of claim 17 further comprises determining the one or more rewards by measuring an overlap between the one or more reasons for study generated by the abstractor and one or more actual reasons for study.

20. One or more non-transitory computer-readable media embodying instructions executable by machine to perform operations, comprising:
- receiving an extractor, an abstractor, an entity linking system and a current history of present illness;
- selecting, using the extractor, one or more sentences from the current history of present illness, wherein the extractor includes a reinforcement learning agent that receives a feedback of one or more rewards from the entity linking system, wherein the one or more rewards are generated by evaluating quality of one or more first reasons for study generated by the abstractor;
- generating, using the abstractor, one or more second reasons for study from the one or more sentences selected by the extractor, wherein the one or more second reasons for study comprise one or more paraphrases of the one or more sentences; and
- predicting, using the entity linking system, one or more diagnoses from the one or more second reasons for study generated by the abstractor.

* * * * *